United States Patent [19]

Siuta et al.

[11] 4,180,587

[45] Dec. 25, 1979

[54] UREYLENE PHENYLENE ANIONIC NAPHTHALENESULFONIC ACIDS AS COMPLEMENT INHIBITORS

[75] Inventors: Gerald J. Siuta, Yonkers; Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 923,743

[22] Filed: Jul. 11, 1978

[51] Int. Cl.$^2$ .................. A61K 31/185; C07C 143/30
[52] U.S. Cl. ..................... 424/315; 260/506
[58] Field of Search .......................... 424/315; 260/506

[56] References Cited

U.S. PATENT DOCUMENTS

| | | | |
|---|---|---|---|
| 4,046,805 | 9/1977 | Bernstein | 424/315 |
| 4,051,176 | 9/1977 | Bernstein | 424/315 |
| 4,087,548 | 5/1978 | Lenhard | 424/315 |

*Primary Examiner*—Anna P. Fagelson
*Attorney, Agent, or Firm*—Claude J. Caroli

[57] ABSTRACT

A method of inhibiting the complement system in a warm-blooded animal which comprises the administration of a ureylenebis-[substituted-phenylenecarbonyl (and sulfonyl) imino-substituted-phenylene carbonylimino-naphthalenetrisulfonic acid, hexaalkali metal salt].

24 Claims, No Drawings

UREYLENE PHENYLENE ANIONIC NAPHTHALENESULFONIC ACIDS AS COMPLEMENT INHIBITORS

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935-938 (1968); Ann. Rev. Medicine, 19, 1-24 (1968); The John Hopkins Med. J., 128, 57-74 (1971); Harvey Lectures, 66, 75-104 (1972); The New England Journal of Medicine, 287, 452-454; 489-495; 545-549; 592-596; 642-646 (1972); Scientific American, 229, (No. 5), 54-66 (1973); Federation Proceedings, 32, 134-137 (1973); Medical World News, Oct. 11, 1974, pp. 53-66; J. Allergy Clin. Immunol., 53, 298-302 (1974); Cold Spring Harbor Conf. Cell Prolifieration 2/Proteases Biol. Control/229-241 (1975); Ann. Review of Biochemistry, 44, 697 (1975); Complement in Clinical Medicine, Disease-a-Month, (1975); Complement, Scope, December 1975; Annals of Internal Medicine, 84, 580-593 (1976); "Complement: Mechanisms and Functions", Prentice-Hall, Englewood Cliffs, N.J. (1976); Essays Med. Biochem., 2, 1-35 (1976); Hospital Practice, 12, 33-43 (1977); Perturbation of Complement in Disease, Chap. 15 in Biological Amplification Systems in Immunology (Ed. Day and Good), Plenum, New York and London (1977); Am. J. Clin. Pathology, 68, 647-659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1-8, 1195, 1358-1364, 1482 (1977).

A variety of substances have been disclosed as inhibiting the complement system, i.e., a complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327-339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415-419; 902-905; 1049-1052; 1053-1056 (1969); Canadian Journal of Biochemistry, 47, 547-552 (1969); The Journal of Immunology, 104, 279-288 (1970); The Journal of Immunology, 106, 241-245 (1971); The Journal of Immunology, 111, 1061-1066 (1973); Biochim. Biophys. Acta, 317, 539-548 (1973); Life Sciences, 13, 351-362 (1973); Journal of Immunology, 113, 584 (1974); Immunology, 26, 819-829 (1974); Journal of Medicinal Chemistry, 17, 1160-1167 (1974); Biochim. Biophys. Res. Comm., 67, 225-263 (1974); Ann. N.Y. Acad. Sci., 256, 441-450 (1975); Journal of Medicinal Chemistry, 19, 634-639, 1079 (1976); Journal of Immunology, 118, 466 (1977); Arch. Int. Pharmacocyn., 226, 281-285 (1977); Biochem. Pharmacol. 26, 325-329 (1977); Journal Pharm. Sci., 66, 1367-1377 (1977); Chem. Pharm. Bull., 25, 1202-1208 (1977); Biochim. Biophys. Acta, 484, 417-422 (1977) and Journal Clin. Microbiology, 5, 278-284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25, (2), 105–108, 25 (3), 179–184 (1977).

It is known that the compound Suramin is moderately active as a complement inhibitor, and possess the structure:

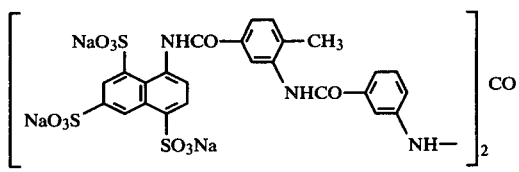

It now has been discovered that certain modifications of this structure provide compounds with enhanced inhibitory activity. This invention is based on such modifications.

The following publications, pertaining to the chemistry of Suramin, are related to the preparation of the novel compounds of this invention:

Bayer & Co., D.R.P. 278,122, June 22, 1913 [C.A. 9, 1096(1915)]
Bayer & Co., D.R.P. 288,272, Jan. 23, 1914 [C.A. 10, 2279(1916)]
Bayer & Co., D.R.P. 288,273, Feb. 21, 1914 [C.A. 10, 2279(1916)]
Frdl. 12, 185–186, 191–195 (1914–1916)
Danish Pat. No. 20,743 (1915)
Austrian Pat. No. 72,298 (1916)
Austrian Pat. No. 72,303 (1916)
U.S. Pat. No. 1,218,654 (1917)
U.S. Pat. No. 1,218,655 (1917)
Austrian Pat. No. 73,381 (1917)
U.S. Pat. No. 1,308,071 (1919)
E. Fourneau, J. Tréfouel, Mme. J. Tréfouel and J. Vallee, Acad. Sci. Comp. Rend., 178, 675–676 (1924)
E. Fourneau, F. Tréfouel and J. Vallee, Ann. de L'Institut Pasteur, 38 (2), 81–114 (1924)
B. Heymann, Zeitschrift Ang. Chem., 37, 585–589 (1924)
British Pat. No. 224,849 (1925)
U.S. Pat. No. 1,606,624 (1926)
J. E. R. McDonagh, Brit. Med. J., 693–696 (1926) [Chem. Zentralblatt, 1769–1770 (1926 II)]
W. Roehl, Arch. Schiff. Trop. Hyg., 30 (1), 103–111 (1926)
Poulenc Frères, D.R.P. 427,857, Apr. 20, 1926 [Frdl. 15, 1434–1436 (1928)]
I. E. Balaban and H. King, J. Chem. Soc., 3068–3097 (1927)
H. Bauer and J. Becker, Arb. Staatsinst. Exptl. Therap., 16 pp. (1928)
U.S. Pat. No. 1,968,820 (1934)
O. Yu. Magidson, O. S. Madaeva and M. V. Rubtzov, Khim. Farm. Prom., 2, 89–94 (1935) [C.A., 30, 4492 (1936)]
U.S. Pat. No. 2,126,180 (1938)
P. Pratsi and L. Raffa, Farmaco Sci e Tec (Pavia), 1, 21–34 (1946)
A. Spinks, Biochem. J., 42, 109–116 (1948)
E. D. Wills and A. Wormall, Biochem. J., 47, 158–170 (1950)
German Pat. No. 890,952 (1953) [C. A. 52, 14693 (1958)]
A. Adams, J. N. Ashley and H. Bader, J. Chem. Soc., 3739–3744 (1956) [C. A. 51, 4375i]

Publications related to the biological use of Suramin compounds for the purpose of inhibiting the complement system, including humans, as determined by the in vivo and in vitro testing of the blood serum of warm-blooded animals are:

B. Stuber and K. Lang, Arch. Exptl. Path. Pharmacol., 154, 41–49 (1930) [C. A. 25, 3067 (1931)]
F. Klopstock, Zeitschrift für Immunitatsforschung und experimentalle Therapie, 75, 348–354 (1932)
H. J. Schmid, Schweiz. Med. Woch., 96, 1267–1269 (1966)
K. Lauenstein, Bayer-Symposium I, 25–30 (1969)
J. S. C. Fong and R. A. Good, Clin. Exp. Immunol., 10, 127–138 (1972)
V. Eisen and C. Loveday, Br. J. Pharmac., 49, 678–687 (1973)
D. Brackertz and F. Kueppers, Allergol. Et Immunopath., 11, 163–168 (1974)
E. Raepple, H-U. Hill and M. Loos, Immunochemistry, 13 (3), 251–255 (1976)

SUMMARY OF THE INVENTION

This invention is concerned with a method of inhibiting the complement system in a warm-blooded animal which comprises administering to said animal a compound selected from those of the formulae:

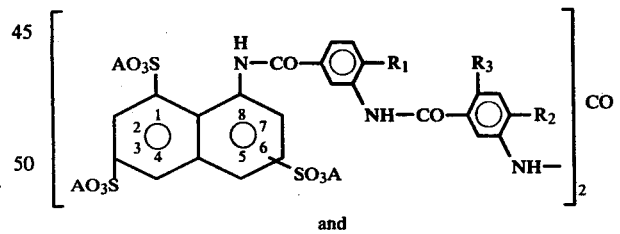

and

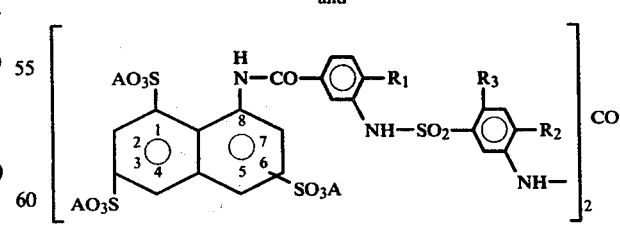

wherein $R_1$, $R_2$ and $R_3$ are selected from the group consisting of hydrogen and methyl; with the proviso that $R_1$, $R_2$ and $R_3$ may not all be hydrogen; with the second proviso that when $R_1$ is methyl, then either $R_2$ or $R_3$ must also be methyl; and A is a pharmaceutically acceptable salt cation.

DESCRIPTION OF THE INVENTION

The amine precursors of the compounds of the invention are prepared by reacting the appropriate 8-amino-1,3,5-(and 1,3,6)-naphthalenetrisulfonic acid, trialkali metal salt with a nitrobenzoyl chloride such as m-nitrobenzoyl chloride and 3-nitro-p-toluoyl chloride, for 1.5–36 hours in an aqueous solution made alkaline with alkali metal hydroxide, anhydrous alkali metal carbonate or alkali metal acetate trihydrate. After neutralization, the solution is diluted with absolute ethanol to provide the corresponding nitro-substituted-phenylenecarbonylimino-1,3,5(and 1,3,6)-naphthalenetrisulfonic acid, trialkali metal salt.

Hydrogenation of the preceding nitro compound trialkali metal salts using 10% palladium-carbon catalyst, filtration, concentration and treatment with absolute ethanol provides the corresponding amino-substituted-phenylenecarbonyliminonaphthalenetrisulfonic acid, trialkali metal salt compounds.

The amino compounds above, dissolved in aqueous media and made alkaline with either alkali metal hydroxide or anhydrous alkali metal carbonate are reacted once more with the desired substituted nitrobenzenesulfonyl chloride or nitrobenzoyl chloride listed above for 1.5–36 hours. After neutralization, the solution is diluted with absolute ethanol to provide the corresponding nitro-substituted-phenylenecarbonyl(and sulfonyl-)imino-substituted-phenylenecarbonyliminonaphthalenetrisulfonic acid, trialkali metal salt.

The amine precursors of the compounds of the invention are then obtained by hydrogenation of the above nitro compounds using 10% palladium-carbon catalyst in water as previously described, filtration and evaporation of the filtrate produces a residue which is dissolved in water and precipitated with absolute ethanol to provide the desired product.

The compounds of the invention, which are active complement inhibitors, are then provided by treatment of the above amine compounds with phosgene in aqueous media made alkaline with alkali metal carbonate or pyridine, neutralization and precipitation from aqueous solution with alcohol.

This invention is concerned with a method of inhibiting the complement system in a body fluid, such as blood serum, which comprises subjecting body fluid complement to the action of an effective complement inhibiting amount of a compound encompassed within the formulae hereinabove. This invention is also concerned with a method of inhibiting the complement system in a warm-blooded animal which comprises administering to said animal an effective complement inhibiting amount of a compound encompassed within the formulae hereinabove. Body fluid can include blood, plasma, serum, synovial fluid, cerebrospinal fluid, or pahtological accumulations of fluid such as pleural effusion, etc.

Compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate complement components as for example, inflammation following coronary occulusion. They may also be useful in the treatment of transplant rejection and as blood culture or transport mediums.

The compounds of the present invention may be administered internally, e.g., orally or parenterally, e.g., intraticularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests code 026, 035, 036, Cap 50, % inhibition and Forssman shock. Table I shows that a compound of the invention possesses highly significant in vitro and in vivo complement inhibiting activity in warm-blooded animals and is more active than the reference compound Suramin. Results obtained are listed in Table I.

TABLE I

| | Biological Activities | | | | In Vivo Activity (Guinea Pig) % Inhibition Intraperitoneal Time (minutes) | | |
|---|---|---|---|---|---|---|---|
| Compound | C1 026* Wells | C-Late 035* Wells | Shunt Inhibition 036* Wells | Cap 50* | 30 | 60 | 120 |
| Suramin | +4** | +2** | — | 361 | −9 | −17 | −44 |
| 8,8'-[Ureylenebis[(4-methyl-3,1-phenylenecarbonyl)imino-(4-methyl-3,1-phenylenecarbonyl)-imino]]di-1,3,5-naphthalenetri- | +3 | +3 | N | 144 | −58 | −65 | −77 |

TABLE I-continued

| | Biological Activities | | | | In Vivo Activity (Guinea Pig) % Inhibition Intraperitoneal Time (minutes) | | |
|---|---|---|---|---|---|---|---|
| Compound | Cl 026* Wells | C-Late 035* Wells | Shunt Inhibition 036* Wells | Cap 50* | 30 | 60 | 120 |
| sulfonic acid, hexasodium salt | | | | | | | |

*Code designation for tests employed as referred herein.
**Activity in wells a serial dilution assay. Higher well number indicates higher activity. The serial dilutions are two-fold.
N = Negative (no activity)

DETAILED DESCRIPTION OF THE INVENTION

The following examples will serve to illustrate the invention in more detail.

EXAMPLE 1

8-[m-(m-Aminobenzamido)benzamido]-1,3,6-naphthalenetrisulfonic acid, trisodium salt A 53.9 g portion of 8-amino-1,3,6-naphthalenetrisulfonic acid, trisodium salt (Eastman) is combined with 120 ml of 1 N sodium hydroxide, 60 ml of water and 45.0 g of m-nitrobenzoyl chloride. The reaction mixture sets up to an unshakable sludge. A 120 ml portion of 1 N sodium hydroxide and 60 ml of water are added and the mixture is shaken for 10–15 minutes. At intervals, two more 120 ml portions of 1 N sodium hydroxide are added and the mixture is shaken 45 minutes after the addition of the last portion. The mixture is acidified with 15 ml of concentrated HCl and extracted copiously with ether. The aqueous phase is filtered through sintered glass and the filtrate is neutralized. The filtrate is concentrated in vacuo at 55°–60° C. to ½ volume, forming a solid. A 200 ml portion of saturated saline and 100 ml of water are added and the mixture is triturated, filtered and washed with 200 ml of saturated saline, two 300 ml portions of 90% ethanol, 400 ml of absolute alcohol and two 300 ml portions of ether giving 71.8 g of 8-m-nitrobenzamido-1,3,6-naphthalenetrisulfonic acid, trisodium salt.

A 50.0 g portion of the product above, in 210 ml of water containing 4.0 g of 10% palladium on carbon catalyst, is hydrogenated at room temperature and an initial pressure of 42 pounds for 4¾ hours. The mixture is filtered. The filtrate is concentrated in vacuo at 55°–60° C. to a low volume, diluted with absolute ethanol, filtered and washed with absolute ethanol, giving 43.06 g of 8-(m-aminobenzamido)-1,3,6-naphthalenetrisulfonic acid, trisodium salt.

A 25.0 g portion of the preceding product, 45 ml of 1 N NaOH, 30 ml of water and 16.5 g of m-nitrobenzoyl chloride are combined and shaken. Three additional 45 ml portions of 1 N NaOH are added with shaking after each portion. The mixture is acidified with 10 ml of concentrated HCl and extracted with seven 150 ml portions of ether. The ether extracts are syphoned off and 200 ml of water is added to solubilize the product. The aqueous phase is neutralized and concentrated in vacuo at 50°–55° C. until a solid precipitates. After standing overnight at room temperature, the mixture is filtered and the solid is washed with 200 ml of saturated saline. The moist paste is dissolved in 50 ml of hot water and diluted with 250 ml of hot absolute alcohol, resulting in a thick paste. The paste is diluted with 100 ml of 80% ethanol and filtered. The solid is slurried on the funnel with 250 ml of absolute alcohol and then filtered giving 25.48 g of 8-[m-(m-nitrobenzamido)benzamido]-1,3,6-naphthalenetrisulfonic acid, trisodium salt.

A 20.0 g portion of the product above, in 160 ml of water containing 2.0 g of 10% palladium on carbon catalyst, is hydrogenated at room temperature and 44 pounds pressure for 3 hours. The catalyst is filtered off and the filtrate is evaporated at 50°–55° C. The resulting oil is diluted with absolute alcohol, triturated, filtered and washed with absolute alcohol giving 17.84 g of the product of the Example.

EXAMPLE 2

8-[3-(3-Amino-p-toluamido)-p-toluamido]-1,3,5-naphthalenetrisulfonic acid, trisodium salt A mixture of 25.0 g of 4-methyl-3-nitrobenzoic acid and 50 ml of thionyl chloride is refluxed for 3½ hours in a 110° C. oil bath. The resulting solution is evaporated in vacuo to an oil. The oil is distilled at a pressure of 0.5 mm of mercury and an oil bath temperature of 145°–160° C. The fraction, bp 108°–113° C., is collected to give 24.3 g of 3-nitro-p-toluoyl chloride.

To a stirred solution of 22.5 g of 8-amino-1,3,5-naphthalenetrisulfonic acid, trisodium salt in 160 ml of water is added 11.0 g of the preceding product with a small amount of ether. Stirring is continued, and after one hour 1.0 g of sodium acetate trihydrate and 1.0 g of 3-nitro-p-toluoyl chloride are added. The mixture is stirred an additional 3 hours and the above addition of sodium acetate and 3-nitro-p-toluoyl chloride is repeated. The mixture is stirred an additional hour, acidified to Congo Red indicator paper with hydrochloric acid and filtered. The filtrate is neutralized with sodium hydroxide, concentrated, dissolved in 50 ml of water and added to one liter of ethanol with stirring for 16 hours. The solid is filtered and forms a gel on washing with ethanol. The gel is dissolved in water and evaporated. The residue is dissolved in 35 ml of hot water and 320 ml of absolute ethanol is added with stirring. The mixture solidifies and water is added to allow filtration. The solid is washed with ether and dried in vacuo. The filtrate is treated by stirring with one liter of ethanol, the separated solid is collected, washed with ether, and dried to yield a combined total of 23.9 g of 8-(3-nitro-p-toluamido)-1,3,5-naphthalenetrisulfonic acid, trisodium salt.

A 22.0 g portion of the preceding product, 200 ml of water and 2.5 g of 10% palladium on carbon catalyst is hydrogenated in a Parr shaker until no additional hydrogen is absorbed. The resulting mixture is filtered through diatomaceous earth, the residue is washed with water, and the filtrate is evaporated, the residue is dissolved in 50 ml of water and added to 900 ml of absolute ethanol. The mixture is warmed on a steam bath and then is stirred at room temperature for 3 hours. The mixture is filtered and the solid is washed with ethanol, then ether and dried in vacuo to give 16.89 g of 8-(3-amino-p-toluamido)-1,3,5-naphthalenetrisulfonic acid, trisodium salt.

To a stirred solution of 3.7 g of the above product, 25.0 ml of water and 670 mg of anhydrous sodium carbonate is added 1.56 g of 3-nitro-p-toluoyl chloride. The mixture is stirred at room temperature for 16 hours. The reaction mixture is filtered, the filtrate is acidified with glacial acetic acid and is evaporated. The residue is dissolved in 20 ml of hot water and ethanol is added. The mixture is heated on a steam bath until solution is achieved then 160 ml of ethanol is added and heating is continued again until solution is complete. The solution is allowed to cool and forms a gelatinous precipitate. The product is collected and is washed with ethanol and ether to yield 4.3 g of 8-[3-(3-nitro-p-toluamido)-p-toluamido]-1,3,5-naphthalenetrisulfonic acid, trisodium salt.

A mixture of 3.0 g of the preceding compound, 125 ml of water and 400 mg of palladium on carbon catalyst is hydrogenated until no additional hydrogen is absorbed. The reaction mixture is filtered through diatomaceous earth and the filtrate is evaporated. The residue is dissolved in hot water and ethanol is added to separate a small amount of black oil. The solution is decanted and ethanol is added to it separating a tan oil. The procedure is repeated several times until no additional oil separates, then the separated oils (excluding the first) are combined and dissolved in 25.0 ml of hot-water. This solution is added to 225 ml of anhydrous ethanol, with vigorous stirring, to form a white precipitate. The product is collected and is washed with ethanol and ether to give 2.88 g of the product of the Example as a white powder.

EXAMPLE 3

8,8'-[Ureylenebis[(4-methyl-3,1-phenylenecarbonyl)imino(4-methyl-3,1-phenylenecarbonyl)imino]]di-1,3,5-naphthalenetrisulfonic acid, hexasodium salt Phosgene is bubbled into a vigorously stirred solution of 2.88 g of the product of Example 2, 25 ml of water and 440 mg of anhydrous sodium carbonate until the solution is acidic to Congo Red indicator paper. The mixture is neutralized with sodium carbonate, then an additional 440 mg of sodium carbonate is added and phosgenation is continued until the mixture is again acidic. The mixture is made alkaline to pH 8.2 with sodium carbonate, then is filtered. The filtrate is evaporated and the residue is dissolved in 20.0 ml of hot water. The slow addition of 80.0 ml of ethanol provides an oil. The mixture is evaporated and the residue is treated as above with 20 ml of hot water and 80 ml of ethanol to yield an oil, then 10 ml of water and 40 ml of ethanol is added and the solution is stirred for 16 hours. A white precipitate suspended in solution is collected by filtration by decanting from a brown gum. The precipitate is washed with ethanol and ether to yield a white powder. Additional white powder is recovered from the above filtrate. The gum is dissolved in water and concentrated, then is heated with 80% aqueous ethanol and is filtered. The ethanol extraction is repeated 3 times, the extracts are combined and evaporated to yield a white solid. The products above are combined and dissolved in 20 ml of hot water. The aqueous solution is added to 180 ml of absolute ethanol with vigorous stirring to provide a precipitate. The precipitate is collected and is washed with ethanol and ether. The product is reprecipitated from water and ethanol, then is collected and washed as above and dried to yield 1.62 g of the product of the Example as a white powder.

EXAMPLE 4

8-[3-(3-Amino-p-toluenesulfonamido)-p-toluamido]-1,3,5-naphthalenetrisulfonic acid, trisodium salt Following the procedure of Example 2, reaction of 3-nitro-p-toluenesulfonyl chloride with 8-(3-amino-p-toluamido)-1,3,5-naphthalenetrisulfonic acid, trisodium salt, followed by reduction with palladium on carbon catalyst provides the product of the Example.

EXAMPLE 5

8,8'-[Ureylenebis[(4-methyl-3,1-phenylenesulfonyl)imino(4-methyl-3,1-phenylenecarbonyl)imino]]di-1,3,5-naphthalenetrisulfonic acid, hexasodium salt Following the procedure of Example 3, reaction of the product of Example 4 with phosgene provides the product of the Example.

EXAMPLE 6

8-[3-(5-Amino-o-toluenesulfonamido)-p-toluamido]-1,3,5-naphthalenetrisulfonic acid, trisodium salt Following the procedure of Example 2, reaction of 5-nitro-o-toluenesulfonylchloride with 8-(3-amino-p-toluamido)-1,3,5-naphthalenetrisulfonic acid, trisodium salt, followed by reduction with palladium on carbon catalyst provides the product of the Example.

EXAMPLE 7

8,8'-[Ureylenebis[(6-methyl-3,1-phenylenesulfonyl)imino(4-methyl-3,1-phenylenecarbonyl)imino]]di-1,3,5-naphthalenetrisulfonic acid, hexasodium salt Following the procedure of Example 3, reaction of the product of Example 6 with phosgene provides the product of the Example.

EXAMPLE 8

8-[3-(5-Amino-2,4-xylenesulfonamido)-p-toluamido]-1,3,5-naphthalenetrisulfonic acid, trisodium salt Following the procedure of Example 2, reaction of 5-nitro-2,4-xylenesulfonyl chloride (from 2-nitro-2,4-xylenesulfonic acid and thionyl chloride) with 8-(3-amino-p-toluamido)-1,3,5-naphthalenetrisulfonic acid, trisodium salt, followed by reduction with palladium on carbon catalyst provides the product of the Example.

EXAMPLE 9

8,8'-[Ureylenebis[(4,6-dimethyl-3,1-phenylenesulfonyl)imino(4-methyl-3,1-phenylenecarbonyl)imino]]di-1,3,5-naphthalenetrisulfonic acid, hexasodium salt Following the procedure of Example 3, reaction of the product of Example 8 with phosgene provides the product of the Example.

EXAMPLE 10

8-[3-(3-Amino-p-toluenesulfonamido)benzamido]-1,3,5-naphthalenesulfonic acid, trisodium salt Following the procedure of Example 2, reaction of 3-nitrobenzoyl chloride with 8-amino-1,3,5-naphthalenetrisulfonic acid, trisodium salt provides 8-(3-nitrobenzamido)-1,3,5-naphthalenesulfonic acid, trisodium salt. Reduction of the latter in water with 10% palladium on carbon catalyst gives the corresponding 3-amino compound. Reaction of this intermediate with 3-nitro-p-toluenesulfonyl chloride followed by reduction with palladium on carbon catalyst provides the product of the Example.

EXAMPLE 11

8,8'-[Ureylenebis[(4-methyl-3,1-phenylenesulfonyl)imino-3,1-phenylenecarbonylimino]]di-1,3,5-naphthalenetrisulfonic acid, hexasodium salt Following the procedure of Example 3, reaction of the product of Example 10 with phosgene provides the product of the Example.

EXAMPLE 12

Preparation of Compressed Tablet

| Ingredient | mg/Tablet |
|---|---|
| Active Compound | 0.5-500 |
| Dibasic Calcium Phosphate N.F. | qs |
| Starch USP | 40 |
| Modified Starch | 10 |
| Magnesium Stearate USP | 1-5 |

EXAMPLE 13

Preparation of Compressed Tablet - Sustained Action

| Ingredient | mg/Tablet |
|---|---|
| Active Compound as Aluminum Lake*, Micronized | 0.5-500 (as acid equivalent) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 14

Preparation of Hard Shell Capsule

| Ingredient | mg/Capsule |
|---|---|
| Active Compound | 0.5-500 |
| Lactose, Spray Dried | qs |
| Magnesium Stearate | 1-10 |

EXAMPLE 15

Preparation of Oral Liquid (Syrup)

| Ingredient | % W/V |
|---|---|
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 16

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 17

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 18

Preparation of Injectable Solution

| Ingredient | % W/V |
|---|---|
| Active Compound | 0.05-5 |
| Benzyl Alcohol N.F. | 0.9 |
| Water for Injection | 100.0 |

EXAMPLE 19

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 20

Preparation of Intra-Articular Product

| Ingredient | Amount |
|---|---|
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-5.7 | |
| Water for Injection qs ad | 100% |

EXAMPLE 21

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 22

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 23

Preparation of Dental Ointment

| Ingredient | % W/W |
|---|---|
| Active Compound | 0.05–5 |
| Petrolatum, White USP qs | 100 |

EXAMPLE 24

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 25

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 26

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 27

Preparation of Spray Lotion (non-Aerosol)

| Ingredient | % W/W |
|---|---|
| Active Compound | 0.05–5 |
| Isopropyl Myristate | 20 |
| Alcohol (Denatured) qs | 100 |

EXAMPLE 28

Preparation of Buccal Tablet

| Ingredient | g/Tablet |
|---|---|
| Active Ingredient | 0.00325 |
| 6 x Sugar | 0.29060 |
| Acacia | 0.01453 |
| Soluble Starch | 0.01453 |
| F.D. & C. Yellow No. 6 Dye | 0.00049 |
| Magnesium Stearate | 0.00160 |
|  | 0.32500 |

The final tablet will weigh about 325 mg. and may be compressed into buccal tablets in flat faced or any other tooling shape convenient for buccal administration.

EXAMPLE 29

Preparation of Lozenge

| Ingredient | g/Lozenge |
|---|---|
| Active Ingredient | 0.0140 |
| Kompact ® Sugar (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
|  | 1.4000 |

The ingredients are compressed into ⅝" flat based lozenge tooling. Other shapes may also be utilized.

We claim:

1. A method of inhibiting the complement system in a body fluid which comprises subjecting said body fluid to the action of an effective complement inhibiting amount of a compound of the formula:

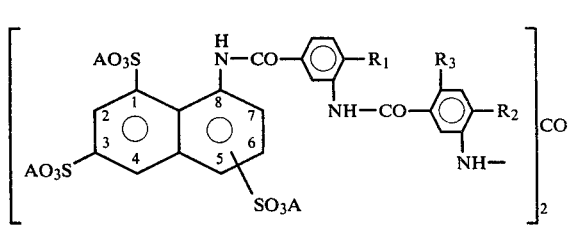

wherein $R_1$, $R_2$, and $R_3$ are selected from the group consisting of hydrogen and methyl; with the proviso that $R_1$, $R_2$ and $R_3$ may not all be hydrogen; with the second proviso that when $R_1$ is methyl, then either $R_2$ or $R_3$ must also be methyl; and A is a pharmaceutically acceptable salt cation.

2. A method according to claim 1 wherein the body fluid is blood serum.

3. A method according to claim 1, wherein the compound is 8,8'-[ureylenebis[(4-methyl-3,1-phenylenecarbonyl)imino(4-methyl-3,1-phenylenecarbonyl)imino]]-di-1,3,5-naphthalenetrisulfonic acid, hexasodium salt.

4. A method of inhibiting the complement system in a warm-blooded animal which comprises administering to said animal an effective complement inhibiting amount of a compound of the formula:

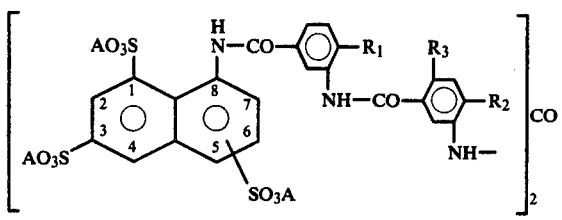

wherein $R_1$, $R_2$ and $R_3$ are selected from the group consisting of hydrogen and methyl; with the proviso that $R_1$, $R_2$ and $R_3$ may not all be hydrogen; with the second proviso that when $R_1$ is methyl, then either $R_2$ or $R_3$ must also be methyl; and A is a pharmaceutically acceptable salt cation.

5. A method according to claim 4, wherein the compound is administered internally.

6. A method according to claim 4, wherein the compound is administered topically.

7. A method according to claim 4, wherein the compound is administered periodontally in the oral cavity.

8. A method according to claim 5, wherein the compound is administered intra-articularly.

9. A method according to claim 4, wherein the compound is 8,8'-[ureylenebis[(4-methyl-3,1-phenylenecarbonyl)imino(4-methyl-3,1-phenylenecarbonyl)imino]]-di-1,3,5-naphthalenetrisulfonic acid, hexasodium salt.

10. A method of inhibiting the complement system in a body fluid which comprises subjecting said body fluid to the action of an effective complement inhibiting amount of a compound of the formula:

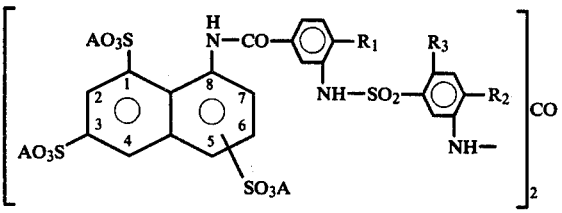

wherein $R_1$, $R_2$ and $R_3$ are selected from the group consisting of hydrogen and methyl; with the proviso that $R_1$, $R_2$ and $R_3$ may not all be hydrogen; with the second proviso that when $R_1$ is methyl, then either $R_2$ or $R_3$ must also be methyl; and A is a pharmaceutically acceptable salt cation.

11. A method according to claim 10, wherein the body fluid is blood serum.

12. A method according to claim 10, wherein the compound is 8,8'-[ureylenebis[(4-methyl-3,1-phenylenesulfonyl)imino(4-methyl-3,1-phenylenecarbonyl)imino]]di-1,3,5-naphthalenetrisulfonic acid, hexasodium salt.

13. A method according to claim 10, wherein the compound is 8,8'-[ureylenebis[(6-methyl-3,1-phenylenesulfonyl)imino(4-methyl-3,1-phenylenecarbonyl)imino]]di-1,3,5-naphthalenetrisulfonic acid, hexasodium salt.

14. A method according to claim 10, wherein the compound is 8,8'-[ureylenebis[(4,6-dimethyl-3,1-phenylenesulfonyl)imino(4-methyl-3,1-phenylenecarbonyl)imino]]di-1,3,5-naphthalenetrisulfonic acid, hexasodium salt.

15. A method according to claim 10, wherein the compound is 8,8'-[ureylenebis[(4-methyl-3,1-phenylenesulfonyl)imino-3,1-phenylenecarbonylimino]]di-1,3,5-naphthalenetrisulfonic acid, hexasodium salt.

16. A method of inhibiting the complement system in a warm-blooded animal which comprises administering to said animal an effective complement inhibiting amount of a compound of the formula:

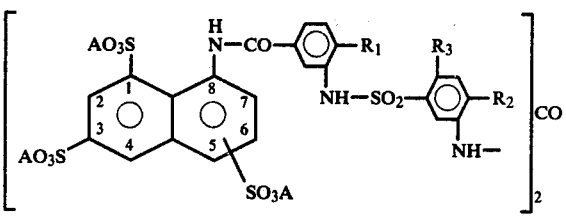

wherein $R_1$, $R_2$ and $R_3$ are selected from the group consisting of hydrogen and methyl; with the proviso that $R_1$, $R_2$ and $R_3$ may not all be hydrogen; with the second proviso that when $R_1$ is methyl, then either $R_2$ or $R_3$ must also be methyl; and A is a pharmaceutically acceptable salt cation.

17. A method according to claim 16, wherein the compound is administered internally.

18. A method according to claim 16, wherein the compound is administered topically.

19. A method according to claim 16, wherein the compound is administered periodontally in the oral cavity.

20. A method according to claim 17, wherein the compound is administered intra-articularly.

21. A method according to claim 16, wherein the compound is 8,8'-[ureylenebis[(4-methyl-3,1-phenylenesulfonyl)imino(4-methyl-3,1-phenylenecarbonyl)imino]]di-1,3,5-naphthalenetrisulfonic acid, hexasodium salt.

22. A method according to claim 16, wherein the compound is 8,8'-[ureylenebis[(6-methyl-3,1-phenylenesulfonyl)imino(4-methyl-3,1-phenylenecarbonyl)imino]]di-1,3,5-naphthalenetrisulfonic acid, hexasodium salt.

23. A method according to claim 16, wherein the compound is 8,8'-[ureylenebis[(4,6-dimethyl-3,1-phenylsulfonyl)imino(4-methyl-3,1-phenylcarbonyl)imino]]di-1,3,5-naphthalenetrisulfonic acid, hexasodium salt.

24. A method according to claim 16, wherein the compound is 8,8'-[ureyelenbis[(4-methyl-3,1-phenylenesulfonyl)imino-3,1-phenylenecarbonylimino]]di-1,3,5-naphthalenetrisulfonic acid, hexasodium salt.

* * * * *